United States Patent [19]
Gillespie

[11] Patent Number: 5,627,054
[45] Date of Patent: May 6, 1997

[54] COMPETITOR PRIMER ASYMMETRIC POLYMERASE CHAIN REACTION

[75] Inventor: David Gillespie, deceased, late of Glenmore, Pa., by Sally Gillespie, executrix

[73] Assignee: The United States of America as represented by the Secretary of the Army, Washington, D.C.

[21] Appl. No.: 628,417

[22] Filed: Apr. 5, 1996

[51] Int. Cl.[6] ................................................ C12P 19/34
[52] U.S. Cl. ............................... 435/91.2; 536/24.3
[58] Field of Search ....................... 435/91.2; 536/24.3

[56] References Cited

PUBLICATIONS

Mentosh et al, "Polymerase Chain Reaction Amplification of Simple–Stranded DNA Containing a Base Analog", Analytical Biochemistry, 1992, 201, 277–281.

Liu et al, Synthesis of a fixed–length single–stranded DNA modes by blocking primer extension in *Bacteriophys M13*, Gene 1986, 42(1), 113–17.

Gyllensten et al., "Generation of single–stranded DNA by the polymerase chain reaction and its application to direct sequencing of the HLA–DQA locus", *Proc. Natl. Acad. Sci. USA*, vol. 85, pp. 7652–7656, Oct. 1988.

Paul D. Siebert et al, "Competitive PCR", *Nature*, vol. 359, pp. 557–558, 8 Oct. 1992.

Shelby L. Berger, "Quantifying $^{32}$P–labeled and Unlabaled Nucleic Acids", *Guide To Molecular Cloning Techniques*, vol. 152, pp. 48–54 (1987).

Michael Becker–André et al, "Absolute mRNA quantification using the polymerase chain reaction (PCR)." A novel approach by a PCR aided transcript assay (PATTY), *Nucleic Acids Research*, vol. 27, No. 22, 1989 (pp. 9437–9446).

G. Gilland et al, "Analysis of cytokine mRNA and DNA: Detection and quantitation by competitive polymerase chain reaction", *Proc. Natl. Acad. Sci. USA*, vol. 87, pp. 2725–2729, Apr. 1990.

Christophe Pannetier et al, "Quantitative titration of nucleic acids by enzymatic amplification reactions run to saturation", *Nucleic Acids Research*, 1993, vol. 21, No. 2 (pp. 577–583).

Vladimir Zachar et al, "Absolute quantification of target DNA: a simple competitive PCR for efficient analysis of multiple samples", *Nucleic Acids Research*, 1993, vol. 21, No. 8 (pp. 2017–2018).

Samer Rifal et al, "Synthetic Exfoliative Toxin A and B DNA Probes for Detection of Toxigenic *Staphylococcus aureus* Strains", *Journal of Clinical Microbiology*, vol. 27, No. 3., Mar. 1989, pp. 504–506.

Otavia L. Caballero et al, "Low stringency–PCR (LS–PCR) allows entirely internally standardized DNA quantitiation", *Nucleic Acids Research*, 1995, vol. 23, No. 1 (pp. 192–193).

James Thompson et al, "A Noise–Free Molecular Hybridization Procedure for Measuring RNA in Cell Lysates", *Analytical Biochemistry* 181, 1989, pp. 371–378.

*Primary Examiner*—Kenneth R. Horlick
*Assistant Examiner*—Joyce Tung
*Attorney, Agent, or Firm*—Ulysses John Biffoni

[57] ABSTRACT

A process for determining both the presence and number of copies of a target nucleic acid sequence in a sample being analyzed. In this process, amplification of a target nucleic acid sequence produces single-stranded DNA that is efficiently detected by nucleic acid probe hybridization and is present in an amount that is proportional to the number of copies of the target sequence originally present in a sample.

10 Claims, 1 Drawing Sheet

5,627,054

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1390 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Staphylococcus aureus ( i x ) FEATURE:
        ( A ) NAME/KEY: primer_bind
        ( B ) LOCATION: complement (165..184)

( i x ) FEATURE:
        ( A ) NAME/KEY: primer_bind
        ( B ) LOCATION: 436..417

( i x ) FEATURE:
        ( A ) NAME/KEY: primer_bind
        ( B ) LOCATION: 360..321
        ( D ) OTHER INFORMATION: /label=0 CAPTUREPROBE ( i x ) FEATURE:
        ( A ) NAME/KEY: primer_bind
        ( B ) LOCATION: 410..389
        ( D ) OTHER INFORMATION: /label= LABELPROBE ( x i ) SEQUENCE DESCRIPTION: SEQ ID NO:1:

```
GGATCCGAAG ATGATTGGGT AAAATTCGAT CAAGTAATTA AAAAGATGG CTACTGGTGG        60

ATTAGATTCA AATATCAACG TGAGGGCTCT AGTACTAACG ATTTTTTTG TGCAGTATGT       120
```

```
AGAATCACTG ACAAGGAACA AAAGATTAAA AATGAAAAAT ATTGGGGAAC TATTGAGTGG    180

AATTAACAAA CGTATTTAAT GTTTAGTTAA TTAAAAGTTA ATAAAAAAAT AATTTGTTTT    240

GAAATAGAAA CGTTATATAA TTTTTAATGT ATTCGAATAC ATTAAAAAAC GCAAATGTTA    300

GGATGATTAA TAATGAATAA TAGTAAAATT ATTTCTAAAG TTTTATTGTC TTTATCTCTA    360

TTTACTGTAG GAGCTAGTGC ATTTGTTATT CAAGACGAAC TGATGCAAAA AAACCATGCA    420

AAAGAGAAGT TTCAGGAGAA GAAATAAAAA AACATGAAGA GAAATGGAAT AAGTACTATG    480

GTGTCAATGC ATTTAATTTA CCAAAGAGC TTTTTAGTAA AGTTGATGAA AAAGATAGAC    540

AAAAGTATCC ATATAATACT ATAGGTAATG TTTTTGTAAA AGGACAAACA AGTGCAACTG    600

GTGTGTTAAT TGGAAAAAAT ACAGTTCTAA CAAATAGACA TATCGCTAAA TTTGCTAATG    660

GAGATCCATC TAAAGTATCT TTTAGACCTT CTATAAATAC AGATGATAAC GGTAATACTG    720

AAACACCATA TGGAGAGTAT GAAGTCAAAG AAATATTACA AGAACCATTT GGTGCAGGTG    780

TTGATTTAGC ATTAATCAGA TTAAAACCAG ATCAAACGG TGTTTCATTA GGCGATAAAA    840

TATCGCCAGC AAAAATAGGG ACATCTAATG ATTTAAAAGA TGGAGACAAA CTCGAATTAA    900

TAGGCTATCC ATTCGATCAT AAAGTTAACC AAATGCACAG AAGTGAAATT GAGTTAACAA    960

CTTTATCAAG AGGATTAAGA TACTATGGAT TTACAGTTCC GGGAAATTCT GGATCAGGTA   1020

TATTTAATTC AAATGGAGAA TTAGTTGGTA TACATTCTAG CAAAGTGTCT CATCTTGATA   1080

GAGAGCATCA AATAAATTAT GGTGTTGGTA TTGGGAATTA TGTCAAGCGC ATTATAAACG   1140

AGAAAAATGA GTAATAAATA AAATAAAAAT CCGTGGATGT TTTATACAAA ACTTATATTT   1200

TATAGCAGTA AGAAGCTGAC TGCATATTTA AACCACCCAT ACTAGTTACT GGGTGGTTGT   1260

TTTTTTATGT TATATTATAA ATGATCAAAC TACACCACCT ATTAATTTAG GAGTGTGGTT   1320

ATTTTAATAT GCGAAGCTAA AATAACTACA AATGATACCA TTTTGATAC CAAAAAATAA   1380

TAGACGGATC                                                          1390
```

( 2 ) INFORMATION FOR SEQ ID NO:2:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: oligodeoxynucleotide ( i i i ) HYPOTHETICAL: NO ( i v ) ANTI-SENSE: NO ( v i ) ORIGINAL SOURCE:
        ( A ) ORGANISM: Staphylococcus aureus ( x i ) SEQUENCE DESCRIPTION: SEQ ID NO:2:

```
GGGAACTATT GAGTGGAATT    20
```

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: oligodeoxynucleotide ( i i i ) HYPOTHETICAL: NO ( i v ) ANTI-SENSE: YES ( v i ) ORIGINAL SOURCE:
    ( A ) ORGANISM: Staphylococcus aureus ( x i ) SEQUENCE DESCRIPTION: SEQ ID NO:3:

```
GCTGAAACTT CTCTTTTGCA          20
```

( 2 ) INFORMATION FOR SEQ ID NO:4:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: oligodeoxynucleotide ( i i i ) HYPOTHETICAL: NO ( i v ) ANTI-SENSE: YES ( x i ) SEQUENCE DESCRIPTION: SEQ ID NO:4:

```
GCTGAAACTT CTCTTTTGCA VHHVV    25
```

( 2 ) INFORMATION FOR SEQ ID NO:5:

( i ) SEQUENCE CHARACTERISTICS:
        ( A ) LENGTH: 140 bases
        ( B ) TYPE: nucleic acid
        ( C ) STRANDEDNESS: single
        ( D ) TOPOLOGY: linear ( i i ) MOLECULE TYPE: oligodeoxynucleotide ( i i i ) HYPOTHETICAL: NO ( i v ) ANTI-SENSE: YES ( x i ) SEQUENCE DESCRIPTION: SEQ ID NO:5:

```
TAGAGATAAA GACAATAAAA CTTTAGAAAT AATTTTACTA AAAAAAAAA AAAAAAAAA    60
AAAAAAAAAA AAAAAAAAAA AAAAAAAAA AAAAAAAAAA AAAAAAAAA AAAAAAAAA    120
AAAAAAAAAA AAAAAAAAAA                                              140
```

( 2 ) INFORMATION FOR SEQ ID NO:6:

( i ) SEQUENCE CHARACTERISTICS:
        ( A ) LENGTH: 240 bases
        ( B ) TYPE: nucleic acid
        ( C ) STRANDEDNESS: single
        ( D ) TOPOLOGY: linear ( i i ) MOLECULE TYPE: oligodeoxynucleotide ( i i i ) HYPOTHETICAL: NO ( i v ) ANTI-SENSE: YES ( x i ) SEQUENCE DESCRIPTION: SEQ ID NO:6:

```
TAGAGATAAA GACAATAAAA CTTTAGAAAT AATTTTACTA AAAAAAAAA AAAAAAAAA    60
AAAAAAAAAA AAAAAAAAAA AAAAAAAAA AAAAAAAAAA AAAAAAAAA AAAAAAAAA    120
AAAAAAAAAA AAAAAAAAAA AAAAAAAAA AAAAAAAAAA AAAAAAAAA AAAAAAAAA    180
AAAAAAAAAA AAAAAAAAAA AAAAAAAAA AAAAAAAAAA AAAAAAAAA AAAAAAAAA    240
```

( 2 ) INFORMATION FOR SEQ ID NO:7:

( i ) SEQUENCE CHARACTERISTICS:

(A) LENGTH: 21 bases
(B) TYPE: nucleic acid
(C) STRANDEDNESS: single
(D) TOPOLOGY: linear (i i) MOLECULE TYPE: oligodeoxynucleotide (i i i) HYPOTHETICAL: NO (i v) ANTI-SENSE: YES (v i) ORIGINAL SOURCE:
    (A) ORGANISM: Staphylococcus aureus (x i) SEQUENCE DESCRIPTION: SEQ ID NO:7:

TTTGCATCAG TTCGTCTTGA A    21

COMPETITOR PRIMER ASYMMETRIC POLYMERASE CHAIN REACTION

GOVERNMENTAL INTEREST

The invention described herein may be manufactured, used and licensed by or for the U.S. Government.

BACKGROUND OF THE INVENTION

1. Field of the Invention

This invention relates generally to the detection of nucleic acid sequences by polymerase chain reaction (PCR). More particularly, this invention relates to a process for efficiently producing single-stranded PCR products in an amount proportional to the amount of a target nucleic acid sequence present in a sample being analyzed.

2. Description of the Art

PCR is a commonly used technique for the detection of target nucleic acid sequences in a sample due to its exquisite specificity and sensitivity. Specificity is achieved by the use of two oligonucleotide primers whose sequences are complementary to sequences that define a deoxyribonucleic acid (DNA) segment containing the target sequence. Following heat denaturation of the target DNA, these primers anneal to their complementary sequences and are extended using a DNA polymerase enzyme and nucleotides. This can be thought of as a symmetrical process: the primers are selected to hybridize to opposite strands of the target sequence in an orientation such that DNA synthesis by the polymerase fills in the region between the primers. Thus, a double-stranded DNA replica, or PCR product, of the original target nucleic acid sequence is produced.

Repetitions of this cycle of denaturation, primer annealing, and extension results in the exponential accumulation of PCR products. This exponential amplification provides the sensitivity of PCR, allowing the detection of extremely small amounts of nucleic acid molecules containing the target sequence, i.e. a single DNA molecule has been amplified and detected. Target sequences in ribonucleic acid (RNA) can also be amplified and detected by performing PCR on complementary DNA (cDNA) produced from an RNA template.

PCR products are generally analyzed by gel electrophoresis or by hybridization with a nucleic acid probe. In many instances, detection of PCR products with nucleic acid probes is the preferred analytical method because it is faster and more economical than gel electrophoresis.

However, analysis of PCR products with nucleic acid probes is a multistep process. First, the double-stranded PCR products are denatured to generate a mixture of single-stranded PCR products. Next, a nucleic acid probe hybridizes to the strand of the mixture that has a sequence complementary to that of the probe to form a probe-PCR product hybrid molecule. Finally, the probe-PCR hybrid is detected.

This process is inefficient because denatured PCR products rapidly renature. That is, the two strands of denatured DNA products quickly reassociate with each other and reform the double-stranded PCR products, thereby excluding the nucleic acid probe. This renaturation problem can be avoided by modifying PCR such that single-stranded DNA of a chosen strand is the major PCR product. A prior art process for producing single-stranded PCR product is asymmetric PCR. (See, e.g., U. B. Gyllensten and H. A. Erlich, "Generation of single-stranded DNA by the polymerase chain reaction and its application to direct sequencing of the HLA-DQA locus." *Proc. Natl. Acad. Sci. USA*, vol. 85, pp. 7652–7656 (1988), herein incorporated by reference.)

Asymmetric PCR uses an unequal, or asymmetric, concentration of the two amplification primers. For example, typical primer ratios for asymmetric PCR are 50:1 to 100:1. During the initial 15 to 25 cycles of asymmetric PCR, most of the product generated is double-stranded and accumulates exponentially. However, as the low-concentration primer becomes depleted, further cycles generate an excess of one strand, i.e., the strand that is complementary to the limiting primer. This single-stranded DNA accumulates linearly resulting in a PCR product mixture that contains both double-stranded DNA and single-stranded DNA. Consequently, renaturation of the double-stranded PCR product is an insignificant factor, since detection of the single-stranded PCR product with a nucleic acid probe is highly efficient.

Besides detecting the presence of a DNA or RNA sequence in a sample, some determinations also require quantifying the number of molecules having the target sequence that are initially present in a sample. For example, quantitative information is required for the analysis of the induction of mRNA in response to exogenous stimuli, gene amplification in tumors and the progress of some viral infections. Quantitative determinations using symmetric PCR are well known in the art. In brief, the quantity of DNA or cDNA in a sample is determined by comparing the amounts of PCR products that result from co-amplification of a target sequence and an added internal standard of known concentration that is amplified by the same primers. (See, e.g., P. D. Seibert and J. W. Larrick, *Nature*, vol. 359, pp. 557–558 (1992), herein incorporated by reference. ) However, as discussed above, symmetric PCR is not a satisfactory method for amplifying target sequences for detection by nucleic acid probe hybridization due to the need for denaturation of the double-stranded PCR products and the complications arising from PCR product reannealing.

Although asymmetric PCR overcomes these deficiencies of symmetric PCR in providing efficient detection, asymmetric PCR is not suitable for quantitative determinations because the amount of single-stranded PCR product generated after amplification is primarily determined by the amount of limiting primer added to the reaction, not by the amount of target DNA or RNA originally present in the sample. For example, increasing quantities of target in the sample results only in fewer cycles being required to exhaust the limiting primer. Thus, quantitation of target sequences amplified by asymmetric PCR is only possible within a 1000-fold range of initial target sequence concentration and even within that range, a 10-fold increase in target produces only a 2-fold increase in detection.

From the foregoing, it will be readily apparent to those skilled in the art that for applications requiring both efficient detection and accurate quantitation of target sequences by nucleic probe hybridization, neither of the :prior art PCR processes discussed above is satisfactory. Therefore, those skilled in the art would appreciate the usefulness of a process that generates a large number of single-stranded copies of a target sequence in an amount that is proportional to the number of target nucleic acid molecules originally present in a sample.

SUMMARY OF THE INVENTION

The present invention provides a new and useful process for determining both the presence and number of copies of a target nucleic acid sequence in a sample being analyzed. In the process of the present invention, amplification of a target nucleic acid sequence produces single-stranded DNA that is efficiently detected and is present in an amount that is proportional to the number of copies of the target sequence originally present in a sample.

In accordance with one embodiment of the, present invention, detection of a target nucleic acid sequence includes a first symmetric PCR phase, i.e. using equal amounts of the amplification primers, followed by a second competitor primer asymmetric PCR phase, wherein an excess of a false, or competitor, primer is added to essentially immediately stop the amplification of a predetermined strand. This competitor primer is capable of preventing one of the amplification primers from annealing to the target sequence but is incapable of serving as a primer for copying the target sequence. The competitor primer is added in a large molar excess over its cognate primer, thus essentially immediately blocking hybridization of, and thereby DNA synthesis from, the cognate primer. After addition of the competitor primer, further PCR cycles are asymmetric, amplifying only one strand. This single-stranded PCR product can be efficiently detected by nucleic acid probe hybridization.

In addition, the above described process; allows the determination of how many nucleic acid molecules containing the target sequence are present in a sample of interest. Amplification of the target sequence by the first symmetric PCR phase yields double-stranded PCR product in an amount that is exponentially proportional to the original amount of target DNA or RNA. The second competitor asymmetric PCR phase yields single-stranded PCR product in an amount that is linearly proportional to the amount of double-stranded PCR product. Therefore, by determining the amount of single-stranded DNA produced, the number of target DNA or RNA molecules originally present in the sample being analyzed can be quantified.

DETAILED DESCRIPTION OF THE INVENTION

One embodiment of the present invention amplifies a DNA segment in a two phase process to produce singlestranded DNA in an amount that is proportional to the starting amount of the nucleic acid segment.

Figure 1:
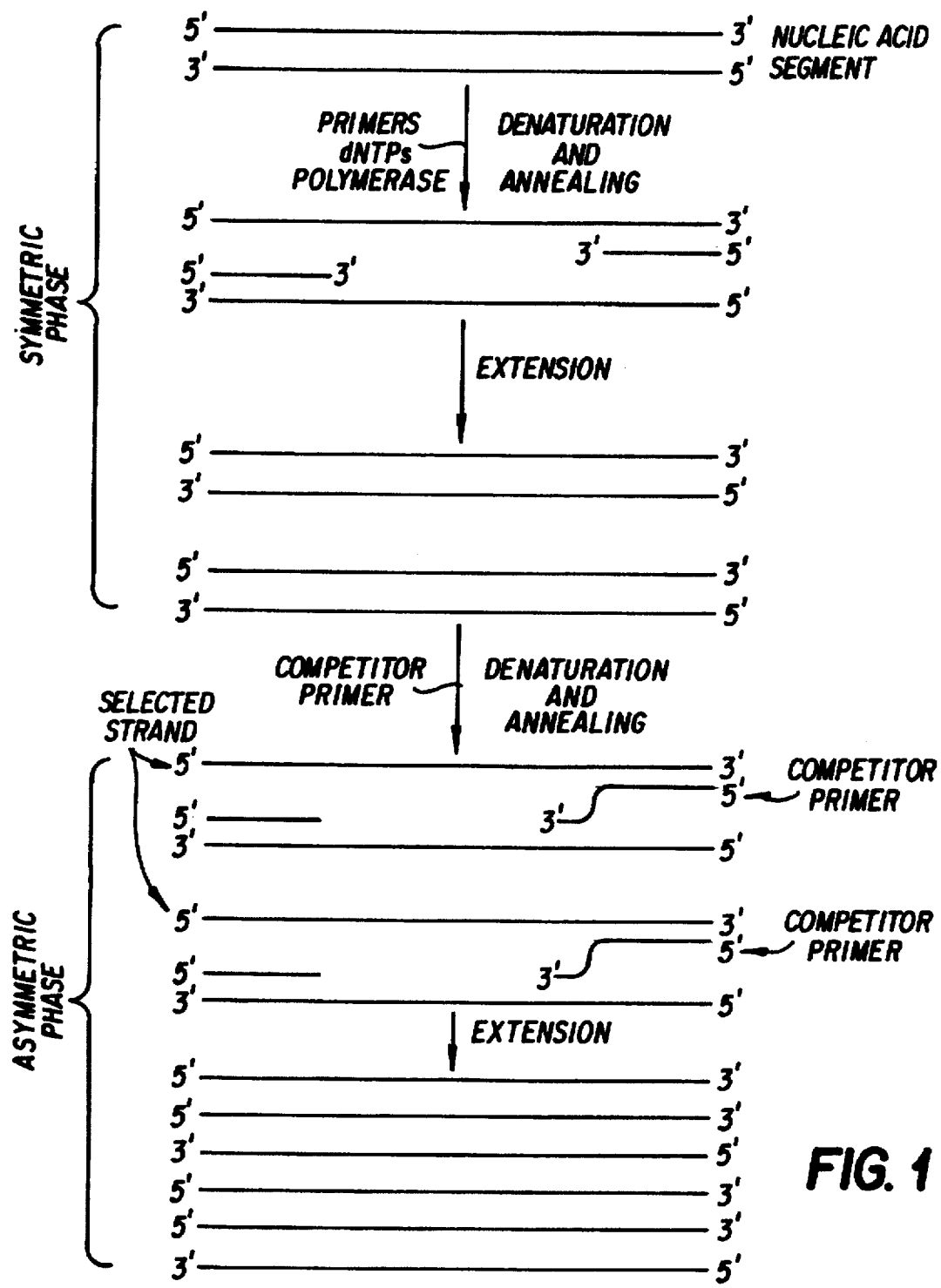
FIG. 1 is a schematic representation of an embodiment of a process according to the invention.

As depicted in FIG. 1, the first phase comprises symmetrically amplifying a nucleic acid segment defined by first and second amplification primers and having two complementary strands via the polymerase chain reaction. The nucleic acid segment is amplified in a reaction mixture containing the amplification primers, deoxyribonucleotides (dNTPs), a reaction buffer and a thermally stable polymerase, preferably a polymerase lacking an inherent 3'–5' exonuclease activity, such as Taq DNA polymerase. Symmetric amplification involves a series of "thermal cycling" steps, including denaturation at 90° to 95° C., preferably 95° C., annealing at 40° to 65° C., the preferred temperature depends on the sequence and length of the amplification primers and is empirically determined, and extension at 65° C. to 75° C., preferably 72° C. The reaction mixture is subjected to 10–50 of such thermal cycles, preferably 40 cycles. This first symmetric amplification phase results in double-stranded DNA product in an amount that is exponentially proportional to the starting amount of the nucleic acid segment.

The second phase is asymmetrical and comprises amplifying a single, selected strand of the double-stranded DNA produced in the symmetric phase. This asymmetric phase is initiated by adding an excess of a competitor primer which essentially immediately prevents the amplification primer that is complementary to the selected strand from annealing thereto. Preferably, the competitor primer is capable of binding to the selected strand at the same site as the complementary amplification primer but is incapable of being extended by polymerase. More preferably, the competitor primer is 20–50 nucleotides in length with a 5' portion complementary to the amplification primer binding site on the selected strand and a 3' noncomplementary portion that cannot anneal to the selected strand (see FIG. 1) and therefore cannot be extended by polymerase. The 3' portion is preferably 5–10 nucleotides in length. The invention also embraces a competitor primer with a sequence that is completely complementary to the amplification primer binding site on the selected strand, but the 3' terminal base is modified such that it cannot serve as a 3'-OH initiation point for polymerase, e.g. such a modified base could be a dideoxynucleotide or a nucleotide having a protecting group on the 3'-OH. As would be appreciated by those of skill in the art, the competitor primer may be readily obtained using commercially available DNA synthesizers or from companies providing custom DNA synthesis services. The second asymmetrical phase produces single-stranded DNA in an amount that is linearly proportional to the amount of doublestranded DNA produced in the first phase.

The single-stranded DNA product can be detected by a variety of means known in the art. For example, a dNTP with a radioactive label can be added to the reaction mixture along with the competitor primer and the amount of singlestranded DNA produced can be determined by a TCA filter assay (see, e.g., Shelby L. Berger, "Quantifying $^{32}$P-Labeled and Unlabeled Nucleic Acids", in *Guide to Molecular Cloning Techniques*, pp. 49–54 (1987) (ed. by Shelby L. Berger & Alan R. Kimmel, herein incorporated by reference)). Alternatively, nonlabeled PCR double and single-stranded product can be filtered through a nitrocellulose membrane where only the single-stranded product will bind followed by probing the bound DNA with a labeled probe.

Quantifying the amount of target nucleic acid sequence can be done by any of the modifications of the method generally known in the art as competitive PCR. See, e.g., M. Becker-André and K. Hahlbrock, *Nucleic Acids Res.*, vol. 17, pp. 9437–9446 (1989), Gillilan et al., *Proc. Nat. Acad. Sci. USA*, vol 87, pp. 2725–2729 (1990), Pannetier et al., *Nucleic Acids Research*, vol 21, pp. 763–764 (1993), and Zachar et al., *Nucleic Acids Res.*, vol. 21, pp. 2017–2018 (1993), each of which is herein incorporated by reference.

In competitive PCR, known amounts of a DNA fragment containing the same primer template sequences as the target is added to a series of PCR reaction tubes containing equal, but unknown, amounts of the sample nucleic acid. This added DNA fragment, or internal control, competes with the sample nucleic acid for primer binding and amplification and is designed to produce a PCR product that can be distinguished from the sample PCR product by size, hybridization, or change in a restriction site. Following PCR, the amount of products generated by the control and sample are compared. The initial amount of sample nucleic acid is determined by calculating how much of the control DNA was required to achieve equal molar amounts of products.

As would be appreciated by those of ordinary skill in the art, these competitive PCR methods can be readily employed to determine the initial amount of sample nucleic acid amplified according to the present invention. For example, co-amplification of a dilution series of known amounts of a control DNA with equal amounts of sample DNA or cDNA by competitor primer asymmetric PCR would result in single-stranded control and sample products in amounts proportional to the amount of control DNA added and amount of sample DNA or cDNA initially present. By plotting the ratio of sample product to control product as a function of the amount of control DNA added, the initial amount of sample nucleic acid can be extrapolated from the point on the curve corresponding to a 1:1 ratio of sample product to control product.

The invention will be further explained and illustrated in and by the following examples.

EXAMPLE 1

Detection of Staphylococcus Exfoliative Toxin A Sequences

Hospitalized infants frequently suffer from skin lesions caused by Staphylococcal exfoliative toxins which are produced by about 5 % of randomly isolated *Staphylococcus aureus* strains. Of the toxigenic *S. aureus* strains, greater than 90% produce exfoliative toxin A (ETA). (See Rifai et al., *J. Clin. Microbiol.*, vol. 27, pp. 504–506 (1989).) The detection of the gene coding for ETA by symmetric PCR, asymmetric PCR, and competitive primer asymmetric PCR will illustrate the features and advantages of the present invention.

METHODS

Amplification Template

The template used for all PCR reactions was a recombinant plasmid containing the ETA gene. The sequence of the sense strand of the ETA gene is shown in SEQ. ID. NO.: 1. The region comprising nucleotides 165–436 of SEQ ID NO. 1 was amplified by symmetric PCR, traditional asymmetric PCR, or competitor primer asymmetric PCR.

Amplification Primers

Primers were oligodeoxynucleotides purchased from Genosys (Woodlands, Tex.). All oligodeoxynucleotides were dissolved in water at 100 µM and stored at −20° C.

The upstream sense primer, ETA-A2, comprised the sequence (5' to 3') GGGAACTATTGAGTGGAATT (SEQ ID NO. 2) which is located between, and includes, nucleotides 165–184 of SEQ ID NO. 1.

The downstream antisense primer, ETA-B, comprised the sequence (5' to 3') GCTGAAACTTCTCTTTTGCA (SEQ ID NO. 3) which is complementary to the sequence of the sense strand located between, and including, nucleotides 436 to 417.

The competitor primer is designed to be able to compete out either the upstream or downstream primer during the primer annealing step and which is incapable of initiating DNA synthesis, thereby blocking amplification of a predetermined strand. In this case, the competitor primer, ETA-B2, comprised the sequence (5' to 3') GCTGAAACT-TCTCTTTTGCAVHHVV (SEQ ID NO. 4), where V was A, C or G and H was A, C or T. Thus ETA-B2, whose first 20 bases match the sequence of the downstream primer ETA-B, can hybridize to the same location on the sense strand as ETA-B, but can not be extended because the 3' pentamer is not complementary to the five nucleotide stretch immediately upstream of this location, i.e., nucleotides 416–412 of SEQ ID NO. 1 which has the sequence (5' to 3') AACCA.

Symmetric PCR

PCR reactions (100 µl) contained 10 µl of 10X PCR reaction buffer (100 mM Tris-HCl, pH 8.3, 1% gelatin), 6 µl of 25 mM $MgCl_2$, 4 µl of dNTP solution (dNTP solution=2.5 mM of each deoxynucleotide triphosphate), 10 molecules of template DNA (or no template in control reactions), 10 µl each of 1 µM solutions of primers ETA-A2 and ETA-B, 1 µl of Taq polymerase (5 U/µl, Perkin-Elmer Cetus, Norwalk, Conn.) and water to 100 µl. PCR reaction mixtures were overlaid with 25 µl of mineral oil and subjected to 40 thermal cycles, each cycle consisting of denaturation at 95° C. for 1 min.; annealing at 49° C. for 2 min.; and extension at 72° C. for 2 min. During the last cycle, the 72° C. extension step was carried out for 10 min. Products of the PCR reactions were analyzed by electrophoretic fractionation of 5 µl aliquots in 8% polyacrylamide gels, which were then stained with ethidium bromide and photographed under UV light (data not shown).

Asymmetric PCR

Asymmetric reaction mixtures were the same as for symmetric PCR, except that the amount of primer ETA-B was reduced, 1 0-fold to a 10 nM final concentration and the amount of ETA-A2 was increased 10-fold to a 1000 nM final concentration. Asymmetric PCR reactions were subjected to 50 thermal cycles, using the same cycling profile described for symmetric PCR.

Competitor Primer Asymmetric PCR

Reaction mixtures were prepared the same, as for symmetric PCR and were subjected to 40 thermal cycles using the same cycling profile described for symmetric PCR. After cycling, the reaction tubes were opened and competitor primer solution (5 µl) was added. Competitor primer solution consisted essentially of 1 µl of 100 µM competitor primer ETA-B2, 1 µl of 10 µM upstream primer ETA-A2, 0.5 µl of 10X PCR buffer (see above), 0.5 µl of Taq polymerase (5 U/µl), and 2 µl of water. The reaction mixtures were then subjected to an additional 10 thermal cycles, using the above-described cycling profile.

Detection of PCR Products

Figure 2:
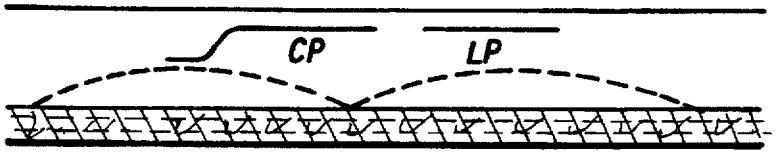
FIG. 2 is a diagrammatic representation of the captureprobe sandwich hybridization assay used to detect and quantify PCR products.

PCR products containing ETA-specific sequences were detected radioactively by a capture system which employs bifunctional captureprobes, labelprobes and affinity membranes in a sandwich hybridization format modified from the procedure described in Thompson et al., *Anal. Biochem.*, vol. 181, pp. 371–378 (1989), herein incorporated by reference. In brief, the bifunctional captureprobe (CP) is an oligodeoxynucleotide capable of binding both to a chosen, or target, strand of the PCR product, and an affinity, or capture membrane (available from RNA Lab, Inc., Exton, Pa.). The labelprobe (LP) contains a radioactive or nonisotopic label and can hybridize to the target PCR product strand at a position adjacent to the captureprobe binding site. Following hybridization of the target strand with both probes in solution, the ternary captureprobe-target-labelprobe complex is then captured on capture membranes (see FIG. 2).

Here, the captureprobe, ETA-CP, has the sequence (5' to 3') TAGAGATAAAGACAATAAAACTTTAGAAATAATT TTACTA$(A)_{100}$ (SEQ ID NO. 5) or TAGAGATAAAGACAATAAAACTTTAGAAATAATTTT ACTA$(A)_{200}$ (SEQ ID NO. 6) and was designed to capture the amplified sense strand onto 10 mm capture membranes through hybridization between the first 40 nucleotides of ETA-CP and nucleotides 360–321 of the ETA gene and through hybridization of the poly(dA) tail on ETA-CP with poly(dT) tails on the capture membranes. The labelprobe comprised a $^{32}$P-end labeled oligodeoxynucleotide having a sequence, (5' to 3') TTTGCATCAGTTCGTCTTGAA (SEQ ID NO. 7), which was complementary to nucleotides 410–389 of SEQ ID NO. 1.

Typically, a 5 μl aliquot of each PCR reaction mixture was added to 10 μl of hybridization solution containing 15 ng of captureprobe (1 pmol) and 4 ng (200,000 cpm) of labelprobe in 6X SSC (900 mM NaCl and 90 mM Na citrate). Hybridization mixtures were incubated at 50° C. for 60 min. Hybridization mixtures containing symmetric PCR aliquots were heat denatured prior to the 50° C. incubation. Following incubation, the hybridization mixtures were transferred to wells containing a capture membrane and 200 μl of NN solution (500 mM NaCl, 1% NP40, 50 mM EDTA, pH 8.0) which were then shaken at room temperature for 15 min. The capture membranes were then rinsed 3 times in NN solution and counted.

RESULTS

Table 1 shows the counts per minute obtained from representative capture membranes used to capture the ternary complex containing the selected, or target, strand of the ETA template which was amplified by symmetric PCR (row A), asymmetric PCR (row B) or competitor primer asymmetric PCR (row C). As seen by comparing the amounts of ETA-CP-target-LP present on the capture membranes in rows A, B, and C, hybridization of the captureprobe and labelprobe to the denatured symmetric PCR product was much less efficient than the hybridization of these probes to the single-stranded PCR products of the asymmetric and competitor primer asymmetric reactions. The relative inefficiency of probing the denatured double-stranded product results from fewer target binding sites available to the probes due to the rapid renaturation of the complementary strands.

TABLE 1

| | PCR | Template + | Template − |
|---|---|---|---|
| A | Symmetric | 1017 | N/A |
| B | Asymmetric | 7363 | 286 |
| C | Competitor Primer Asymmetric | 9483 | 113 |

It will be appreciated that the instant specification is set forth by way of illustration and not limitation, and that various modifications and changes may be made without departing from the spirit and scope of the present invention.

What is claimed is:

1. A process for amplifying an unknown or known staffing amount of a double-stranded nucleic acid segment having first and second complementary strands to produce single-stranded nucleic acid in an amount that is proportional to the starting amount of the nucleic acid segment, which comprises:
   (a) symmetrically amplifying the nucleic acid segment to generate a double-stranded nucleic acid product in an amount that is proportional to the starting amount of the nucleic acid segment, wherein the symmetrical amplifying is carried out by thermal cycling a reaction mixture comprising:
      (i) the nucleic acid segment,
      (ii) a first primer for annealing to the first complementary strand at a first primer specific binding site,
      (iii) a second primer, which is different from the first primer, for annealing to the second complementary strand at a second primer specific binding site,
      (iv) a nucleotide for each of adenine, guanine, cytosine and thymine,
      (v) a reaction buffer, and
      (vi) a thermally stable polymerase for extending annealed primers,
   (b) asymmetrically amplifying the double-stranded nucleic-acid product to generate a single-stranded nucleic acid product in an amount that is proportional to the amount of double-stranded product generated by the symmetrical amplifying, wherein the asymmetrical amplifying comprises:
      (i) adding a competitor primer to the reaction mixture, wherein the competitor primer prevents one of the first and second primers from annealing to the first or second complementary strands and is incapable of being extended by the polymerase, and
      (ii) continuing the thermal cycling.

2. A process according to claim 1, wherein the reaction mixture at the completion of the symmetrical amplifying step contains approximately equal molar amounts of each of the first and second primers and an amount of the competitor primer is added in the asymmetrical amplifying step to exceed this molar amount.

3. A process according to claim 2, wherein the competitor primer is capable of annealing to at least the 5' end of one of the first primer-specific and second primer-specific binding sites.

4. A process according to claim 3, wherein the competitor primer has a 5' complementary portion for annealing to one of the first primer-specific and second primer-specific binding sites and a 3' noncomplementary portion for preventing extension of the competitor primer by the polymerase, and the polymerase lacks a 3' to 5' exonuclease activity.

5. A process according to claim 4, wherein the 5' complementary portion comprises about 20 to 40 bases in length and the 3' noncomplementary portion comprises about 5 to 10 bases in length.

6. A process according to claim 3, wherein said competitor primer has a 3' terminal modified base capable of annealing to the 5' end of one of the first primer-specific and second primer-specific binding sites and which is not a substrate for the polymerase.

7. A process according to claim 6, wherein the 3' terminal modified base is a dideoxynucleotide.

8. A process according to claim 1, wherein said thermal cycling during said symmetrical amplifying step comprises 20 to 50 cycles of denaturation at 90° to 95° C., annealing at 40° to 65° C., and extension at 65° C. to 75° C., and said thermal cycling during said asymmetrical amplifying step comprises 5 to 20 cycles of denaturation at 90° to 95 ° C., annealing at 40° to 65° C., and extension at 65° C. to 75° C.

9. A process according to claim 1, wherein the nucleic acid segment is DNA, the nucleotide for each of adenine, guanine, cytosine and thymine is a deoxyribonucleotide, and the thermally stable polymerase is a DNA polymerase.

10. A process according to claim 9, wherein the DNA polymerase is Taq DNA polymerase.

* * * * *

UNITED STATES PATENT AND TRADEMARK OFFICE
CERTIFICATE OF CORRECTION

PATENT NO. : 5,627,054
DATED : May 6, 1997
INVENTOR(S) : Gillespie, David

It is certified that error appears in the above-indentified patent and that said Letters Patent is hereby corrected as shown below:

In column 13, line 20, "staffing" has been changed to - - starting - -.

Signed and Sealed this

Nineteenth Day of August, 1997

*Attest:*

BRUCE LEHMAN

*Attesting Officer*     *Commissioner of Patents and Trademarks*